United States Patent
Bruning et al.

(10) Patent No.: US 11,690,869 B2
(45) Date of Patent: Jul. 4, 2023

(54) METHODS OF INHIBITING ENVELOPED VIRUSES USING LOW MOLECULAR WEIGHT HYDROPHOBICALLY MODIFIED POLYMERS

(71) Applicant: Johnson & Johnson Consumer Inc., Skillman, NJ (US)

(72) Inventors: Elizabeth Bruning, Skillman, NJ (US); Kimberly Capone, Skilllman, NJ (US); Lisa Renee Gandolfi, Skillman, NJ (US); Anthony Robert Geonnotti, III, Skillman, NJ (US); Euen Thomas Ekman-Gunn, Skillman, NJ (US); Diana Roshek Johnson, Skillman, NJ (US); Frank J. Kirchner, Skillman, NJ (US); Selina Moses, Skillman, NJ (US); Delores Santora, Skillman, NJ (US); Russel Walters, Skillman, NJ (US); Frank C. Sun, Skillman, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/856,766

(22) Filed: Apr. 23, 2020

(65) Prior Publication Data
US 2021/0330699 A1    Oct. 28, 2021

(51) Int. Cl.
    *A61K 31/78*    (2006.01)
(52) U.S. Cl.
    CPC ..................... *A61K 31/78* (2013.01)

(58) Field of Classification Search
    CPC ....... A61K 31/78; A61K 31/085; A61P 31/12; A61P 31/14; A61P 31/18; A61P 31/20; A61P 31/22
    See application file for complete search history.

(56) References Cited

U.S. PATENT DOCUMENTS

| | | |
|---|---|---|
| 3,755,560 A | 8/1973 | Dickert et al. |
| 4,421,769 A | 12/1983 | Dixon et al. |
| 6,433,061 B1 | 8/2002 | Marchant et al. |
| 7,157,414 B2 | 1/2007 | Librizzi et al. |
| 7,803,403 B2 | 9/2010 | Librizzi et al. |
| 7,892,525 B2 | 2/2011 | Faivre et al. |
| 8,025,902 B2 | 9/2011 | Librizzi et al. |
| 8,293,845 B2 | 10/2012 | Tamareselvy et al. |
| 8,329,626 B2 | 12/2012 | Gunn et al. |

(Continued)

FOREIGN PATENT DOCUMENTS

| | | | |
|---|---|---|---|
| EP | 0 859 547 | * | 9/2003 |
| WO | WO 2005/074947 A2 | | 8/2005 |

OTHER PUBLICATIONS

Halder, J et al (PNAS, vol. 103, #47, pp. 17667-17671, 2006 <br>.*

(Continued)

*Primary Examiner* — Gollamudi S Kishore

(57) ABSTRACT

This invention relates to methods and compositions for inhibiting the transmission of enveloped viruses, which entails applying a composition containing a low molecular weight hydrophobically-modified polymer to an infectable or ingestible surface that may contain viruses, wherein said compositions further comprise less than about 9% by weight of surfactant having an HLB of greater than 12.

14 Claims, 3 Drawing Sheets

(56) References Cited

U.S. PATENT DOCUMENTS

| | | | |
|---|---|---|---|
| 8,329,627 B2 | 12/2012 | Gunn et al. | |
| 8,343,902 B2* | 1/2013 | Walters | A61K 8/8147 |
| | | | 510/130 |
| 9,068,148 B2 | 6/2015 | Tamareselvy et al. | |
| 9,931,290 B2 | 4/2018 | Tamareselvy et al. | |
| 10,435,308 B2 | 10/2019 | Man et al. | |
| 10,517,806 B2 | 12/2019 | Emiru et al. | |
| 2006/0166345 A1* | 7/2006 | Gaillac | A61K 48/00 |
| | | | 435/235.1 |
| 2010/0029547 A1* | 2/2010 | Bewley | C07K 14/195 |
| | | | 536/127 |
| 2010/0282409 A1* | 11/2010 | Hobbs | A61P 31/10 |
| | | | 156/327 |
| 2012/0093763 A1* | 4/2012 | Akamine | A61P 31/16 |
| | | | 424/78.27 |
| 2014/0234249 A1 | 8/2014 | Capone et al. | |
| 2016/0262999 A1 | 9/2016 | Pedersen et al. | |
| 2018/0051411 A1* | 2/2018 | Hayashi | A01N 61/00 |

OTHER PUBLICATIONS

Teisser, E., et al in Molecultes, vo. 16, pp. 221-250, 2011.*

Menachery et al., Pathogenic Influenza Viruses and Coronaviruses Utilize Similar and Contrasting Approaches to Control Interferon-Stimulated Gene Responses, American Society of Microbiology, 2014, 5(3): 1-11.

Li, Structure, Function and Evolution of Coronavirus Spike Proteins, Annu. Rev. Virul. 2016, 3(1):237-261.

Sagarin, Cosmetics, Science and Technology, 2nd Edition, vol. 1, pp. 32-43 (1972) and the International Cosmetic Ingredient Dictionary and Handbook, eds. Wenninger and McEwen, pp. 1656-1661, 1626, and 1654-55 (The Cosmetic, Toiletry, and Fragrance Assoc., Washington, D.C., 7th Edition, 1997) (hereinafter "ICI Handbook").

Sagarin, Cosmetics, Science and Technology, 2nd Edition, vol. 1, pp. 72-73 (1972) and the ICI Handbook pp. 1693-1697.

McCutcheon's Detergents and Emulsifiers, North American Edition, pp. 317-324 (1986), and the ICI Handbook, pp. 1673-1686.

Mintel Report Record ID No. 1867920; Neutrogena Ultra Gentle Daily Care Face Cleanser; Date Published Sep. 2012.

Mintel Report Record ID No. 5114245; Johnson's baby moisture wash; Date Published Sep. 2017.

Mintel Report Record ID No. 2165545; Johnson's baby Head-to-Toe washcloths; Published Sep. 2013.

NIH Report; Vaccine Company Develops Nasal Antiseptic That Kills Coronavirus in Lab Studies; https://projectreporter.nih.gov/Reporter_Viewsh.cfm?sl=14E8CD0F4B8AC3D17598B8961CAA4A01A2FFCEB861BF; dated Jun. 30, 2020.

Robertson et al. (Mar. 1995). "Recombination in AIDS viruses." Journal of Molecular Evolution. 40 (3): 249-59.

Liu et al., Research and Development on Therapeutic Agents and Vaccines for COVID-19 and Related Human Coronavirus Diseases, ACS Cent. Sci. 2020, 6, 315-331).

Blaising et al., Arbidol as a broad-spectrum antiviral: An update, Antiviral Research, 107 (2014) 84-94.

Kadam et al., Structural basis of influenza virus fusion inhibition by the antiviral drug Arbidol, PNAS Jan. 10, 2017 114 (2) 206-214.

International Search Report, Application No. PCT/IB2021/053203, dated Jun. 23, 2021.

\* cited by examiner

METHODS OF INHIBITING ENVELOPED VIRUSES USING LOW MOLECULAR WEIGHT HYDROPHOBICALLY MODIFIED POLYMERS

FIELD OF THE INVENTION

The method of this invention relates to the use of low molecular weight hydrophobically modified polymers to inhibit the transmission of viruses known as "enveloped" viruses. It also relates to compositions containing said low molecular weight hydrophobically modified polymers capable of inhibiting transmission of said viruses.

BACKGROUND OF THE INVENTION

Infections due to enveloped viruses cause common diseases such as herpes simplex, HIV/AIDS, hepatitis B, influenza, chicken pox, shingles, small pox, and respiratory infections. While the seriousness of these diseases can range from moderately bothersome to life-threatening, these infections adversely affect the quality of life of its host and the personal, institutional and economic areas of our society. As a result, there have been substantial efforts to develop means to prevent viral infection and its spread. These efforts are complicated by viral diversity, the numerous means by which viruses are transmitted, including: direct contact, exchange of bodily fluids (e.g. saliva, sexual transmission, breast feeding), and aerosol transmission (e.g. coughing, sneezing, etc.) as well as the highly evolved measures by which viruses escape detection and/or eradication by their hosts. There have been numerous successes in the discovery and commercialization of antiviral agents administered to those who have been infected with a virus. However, these treatments often require medical prescriptions, have unwanted side effects, only work on a narrow range of viral types/strains, and/or have limited efficacy. Topically delivered antiviral treatments must also be non-irritating to the treated tissues, or risk increasing the risk of infection.

Therefore, cost effective and gentle agents with potent, broad-spectrum anti-viral activity which are capable of significantly reducing virus transmission would fill an unmet need in the antiviral armamentarium and help prevent the spread of viral infections, especially if mild properties of such agents could permit and encourage widespread, frequent usage due to superior compatibility with skin, eyes and other mucosal membranes.

Viruses have high mutation and replication rates; these properties allow rapid evolution in response to external selective pressures (i.e. drug), often leading to treatment resistance and relapse. The concern of resistance is especially salient when the antiviral compound targets a specific epitope on the virion. Due to high levels of viral genetic diversity, this narrow specificity also usually limits the range of viruses sensitive to the compound. Alternatively, other topical antiviral treatments, such as surfactants, target non-specific viral regions and are broadly effective at neutralizing diverse viruses, however, these are often irritating and toxic to human cells. Treatments that irritate tissues may result in an increased infection rate; damaging cellular membranes increases their permeability to some types of viral particles.

Thus, a non-irritating yet highly effective means for eradicating viruses and significantly reducing their transmission potential would be highly desirable.

Most viruses (e.g., HIV and many animal viruses) have viral envelopes as their outer layer at the stage of their life-cycle when they are between host cells. Robertson et al. (March 1995). "Recombination in AIDS viruses." Journal of Molecular Evolution. 40 (3): 249-59. Some enveloped viruses also have a protein layer called a capsid between the envelope and their genome. Id. The envelopes are typically derived from portions of the host cell membranes (phospholipids and proteins), but include some viral glycoproteins. They may help viruses avoid the host immune system. Glycoproteins on the surface of the envelope serve to identify and bind to receptor sites on the host's membrane. The viral envelope then fuses with the host's membrane, allowing the capsid and viral genome to enter and infect the host.

The cell from which the virus itself buds will often die or be weakened and shed more viral particles for an extended period. The lipid bilayer envelope of these viruses is relatively sensitive to desiccation, heat, and detergents; therefore these viruses are easier to sterilize than non-enveloped viruses, have limited survival outside host environments, and typically transfer directly from host to host. Enveloped viruses possess great adaptability and can change in a short time in order to evade the immune system. Enveloped viruses can cause persistent infections.

Classes of enveloped viruses that contain human pathogens include, e.g., DNA viruses such as Herpesvirus, Poxviruses, Hepadnaviruses, Asfarviridae; RNA viruses such as Flavivirus, Alphavirus, Togavirus, Coronavirus, Hepatitis D, Orthomyxovirus, Paramyxovirus, Rhabdovirus, Bunyavirus, Filovirus; and Retroviruses such as HIV.

COVID-19

Coronaviruses (CoVs) are relatively large viruses containing a single-stranded positive-sense RNA genome encapsulated within a membrane envelope. The viral membrane is studded with glycoprotein spikes that give coronaviruses their crownlike appearance. (See FIG. 1, taken from Liu et al., Research and Development on Therapeutic Agents and Vaccines for COVID-19 and Related Human Coronavirus Diseases, ACS Cent. Sci. 2020, 6, 315-331). While coronaviruses infect both humans and animals, certain types of animals such as bats that host the largest variety of coronaviruses appear to be immune to coronavirus-induced illness. There are four classes of coronaviruses designated as alpha, beta, gamma, and delta. The betacoronavirus class includes severe acute respiratory syndrome (SARS) virus (SARS-CoV), Middle East respiratory syndrome (MERS) virus (MERS-CoV), and the COVID-19 causative agent SARS-CoV-2. Similar to SARS-CoV and MERS-CoV, SARS-CoV-2 attacks the lower respiratory system to cause viral pneumonia, but it may also affect the gastrointestinal system, heart, kidney, liver, and central nervous system leading to multiple organ failure. Current information indicates that SARSCoV-2 is more transmissible/contagious than SARS-CoV.

A number of studies have focused on elucidation of virus structure, virus transmission mechanisms/dynamics, as well as identification of antiviral agents and accurate diagnostics for virus detection. These trends reflect immense interest and desire from the scientific community, including both academic and industrial organizations as well as clinicians, to identify new methods to halt the progression of this epidemic disease and to prevent infection and transmission in the future.

COVID-19 is caused by SARS-CoV-2, a new type of coronavirus in the same genus as SARS-CoV and MERS-CoV. Viral proteins responsible for SARS-CoV-2 entry into host cells and replication are structurally similar to those associated with SARS-CoV. Thus, research and development on SARS and MERS may offer insights that would be beneficial to the development of therapeutic and preventive agents for COVID-19.

Arbidol, CAS No. 131707-23-8, which targets S protein/ACE2, is an inhibitor that may disrupt the binding of the viral envelope protein to host cells and prevent entry of the virus to the target cell has entered into clinical trials for treatment of COVID-19. See Liu et al. above and FIG. 2 below, taken from Blaising et al., Arbidol as a broad-spectrum antiviral: An update, Antiviral Research, 107 (2014) 84-94. See also Kadam et al., Structural basis of influenza virus fusion inhibition by the antiviral drug Arbidol, PNAS Jan. 10, 2017 114 (2) 206-214.

The 2003 emergence of the severe acute respiratory disease coronavirus (SARS-CoV) demonstrated that CoVs are capable of causing outbreaks of severe infections in humans. A second severe CoV, Middle East respiratory syndrome coronavirus (MERS-CoV), emerged in 2012 in Saudi Arabia. More recently, COVID-19 identified in Wuhan, China, in December 2019, has proven particularly detrimental.

Given that the polymers of the invention have shown activity against enveloped viruses, it is expected that polymers of the invention may also show activity against COVID-19 by inhibiting entry of the virus in a host cell. See FIG. 3.

RetroVirox, San Diego, Calif., has developed cell-based assays that can be used to evaluate experimental treatments against coronaviruses, including SARS-CoV-2. The Company provides testing with SARS-CoV-2 pseudoviruses to evaluate entry inhibitors against the novel coronavirus causative agent of COVID-19. The pseudovirus assay utilizes HIV pseudoviruses coated with the viral spike (S) protein of SARS-CoV-2 (Wuhan isolate). The assay, which recapitulates the mode of entry of the novel coronavirus, it can be used for, e.g., evaluate small-molecule entry inhibitors targeting the S viral protein, the ACE-2 viral receptor, or host proteases and other targets involved in SARS-CoV-2 viral entry.

U.S. Pat. Nos. 7,803,403 and 8,025,902 to Johnson & Johnson Consumer Inc. disclose personal care compositions that contain a low molecular weight, non-cross linked, linear acrylic copolymer and at least one surfactant; and a method of cleansing using said personal care compositions.

U.S. Pat. Nos. 8,343,902 and 8,329,626 to Johnson & Johnson Consumer Inc. disclose a skin cleansing composition that comprises a low molecular weight, non-crosslinked, linear acrylic copolymer and a non-ethoxylated anionic surfactant.

U.S. Pat. No. 8,329,627 to Johnson & Johnson Consumer Inc. discloses a clear skin cleansing composition that comprises a low molecular weight, non-crosslinked, linear acrylic copolymer and a blend of at least two amphoteric surfactants.

U.S. Pat. No. 8,293,845 to Lubrizol Corp. discloses a method for increasing the critical micelle concentration of a surfactant composition comprising including a linear hydrophobically modified (meth)acrylic polymer in said composition.

U.S. Pat. No. 7,892,525 to Lubrizol Advanced Materials, Inc. discloses antiperspirant compositions that comprise a cationic hydrophobically modified polymeric gelling agent and an acidic antiperspirant compound.

U.S. Pat. No. 9,068,148 to Lubrizol Advanced Materials, Inc. discloses an acrylic polymer blend that comprises at least one crosslinked acrylic copolymer and at least one acrylic linear, non-crosslinked polymer; a method for making the acrylic polymer blend; and method for thickening an aqueous composition comprising the acrylic polymer blend.

U.S. Pat. No. 9,931,290 to Lubrizol Advanced Materials, Inc. discloses a surfactant composition that comprises a surfactant and a crosslinked acrylic copolymer; and a personal care cleansing composition comprising the surfactant composition.

U.S. Pat. No. 10,517,806 to Ecolab USA Inc. claims a foaming antimicrobial dermal cleanser that comprises a cationic active ingredient; a cationic compatible surfactant; a foam boosting agent; a foam structure enhancing agent; a skin conditioning agent; and water. The reference claims a method of reducing bacterial, microbial, fungicidal, or viral population on a dermal tissue of a mammal comprising contacting the dermal tissue with the foaming antimicrobial dermal cleanser. The reference also discloses that cationic active ingredients are antimicrobial agents useful in the present invention and that the foam structure enhancing agent can be polyethyleneglycol. The reference discloses the use of *S. aureus* and *Escherichia coli* as test microbial cultures to test microbial efficacy of the formulas therein.

U.S. Pat. No. 10,435,308 to Ecolab USA, Inc. claims a composition for improving oil removal from an oil/aqueous phase solution by foam fractionation that comprises an associative thickener; a surfactant comprising a sorbitan ester; and a viscoelastic surfactant, wherein the viscoelastic surfactant is a betaine, amine oxide, and/or ethoxylated fatty amine. The reference discloses that the composition may be used in, e.g., cleaning agents, cosmetics, pickles, aqueous pigment pastes, automotive finishes, industrial coatings, printing inks, lubricating greases, plaster paints and wall paints, textile coatings, pharmaceutical preparations, crop protection formulations, filler dispersions, adhesives, detergents, wax dispersions, polishes, auxiliaries for tertiary mineral oil production etc.

U.S. Published Application No. 20160262999 to Ecolab USA, Inc. claims an antimicrobial dermal concentrate that comprises a cationic active ingredient; a foam boosting surfactant; a foam boosting copolymer; a foam stabilizing structure; and water. The reference claims that the concentrate can be used to reduce bacterial, microbial, fungicidal or viral population on a dermal tissue of a mammal. The reference discloses that cationic active" is the ingredient that provides antimicrobial activity. The reference discloses that the concentrate may contain a skin conditioner such as polyethylene glycol.

Menachery et al., Pathogenic Influenza Viruses and Coronaviruses Utilize Similar and Contrasting Approaches To Control Interferon-Stimulated Gene Responses, American Society of Microbiology, 2014, 5(3): 1-11, discloses that influenza viruses and coronaviruses exhibit differences in terms of replication, immune stimulation, and overall lethality.

Li, Structure, Function and Evolution of Coronavirus Spike Proteins, Annu. Rev. Virul. 2016, 3(1):237-261, discusses the evolution of two critical functions of coronavirus spike proteins, receptor recognition and membrane fusion, in the context of the corresponding functions from other viruses and host cells.

The cited references are incorporated by reference in their entirety herein.

Neutrogena Corp, Los Angeles, Calif., markets and sells a Neutrogena® Ultra Gentle Daily Cleanser product that contains the use of potassium acrylates copolymer as a viscosity increasing agent.

Johnson & Johnson Consumer Inc. markets and sells products, including Johnson's Head to Toe Baby Wash; Johnson's Baby Moisture Wash; and Johnson's Baby Wipes that contain the use of potassium acrylates copolymer as a viscosity increasing agent.

Hand sanitizers are generally used to decrease infectious agents on the hands. They are available as liquids, gels, and foams. Alcohol-based versions and non-alcohol based versions are available. Alcohol-based versions typically contain some combination of isopropyl alcohol, ethanol (ethyl alcohol), or n-propanol, with versions containing 60% to 95% alcohol being the most effective. Care should be taken as they are flammable. Alcohol-based hand sanitizer works against a wide variety of microorganisms. Non-alcohol based versions, which typically contain benzalkonium chloride or triclosan, are less effective than alcohol-based ones.

In 2020, BlueWillow Biologics, Inc. launched NanoBio Project nasal antiseptic solution containing OTC monograph benzalkonium chloride. The product is applied by thoroughly swabbing the skin inside of each nostril.

SUMMARY OF THE INVENTION

This invention relates to a method of inhibiting entry of enveloped viruses into cells comprising, consisting essentially of and consisting of contacting said viruses with an anti-viral composition comprising at least one low molecular weight hydrophobically modified polymer in an amount effective to inhibit entry of these viruses into cells.

Surprisingly, we have found that low concentrations of certain low molecular weight hydrophobically modified polymers known for their gentle properties are able successfully to inhibit entry of enveloped viruses into host cells and thus inhibit transmission of viruses to the hosts.

We believe that these polymers would not encounter or engender some of the historical problems with antiviral treatments, such as drug resistance, narrow breadth of neutralization and host cellular toxicity. The low molecular weight hydrophobically modified polymers useful in the methods and compositions of this invention are broadly active against several viral types and across multiple viral strains. Additionally, these polymers work through a non-specific mechanism of entry inhibition, thereby increasing their chances for inhibitory success and decreasing the likelihood of resistance. Furthermore, as these polymers are exceptionally gentle on mucosal tissues, they have little or no toxicity to human tissues.

Our bodies are challenged by viruses on a daily basis and our immune system, including our skin barrier, is designed to minimize the number of viruses that reach infectable surfaces. The low molecular weight hydrophobically modified polymers useful in the methods and compositions of this invention block the ability of the virus to bind to and/or enter cells, thereby reducing the probability that an infectious virus can reach a target cell and cause a systemic infection. Viral infection is partially the result of a stochastic process—the more viruses that come in contact with infectable cells, the more likely that tissue is to be infected—therefore, use of these polymers to block infectious viruses benefits the immune system, further reduces chances of infection and promotes general good health. The methods and compositions of this invention using low molecular weight hydrophobically modified polymers are surprisingly effective at reducing the number of infectious virions across a broad range of viral types and strains while remaining gentle and non-irritating to human tissues.

The disclosure may best be understood by reference to the following description taken in conjunction with the accompanying figures, which illustrate particular embodiments.

DETAILED DESCRIPTION OF THE PREFERRED EMBODIMENTS

Figure 1:
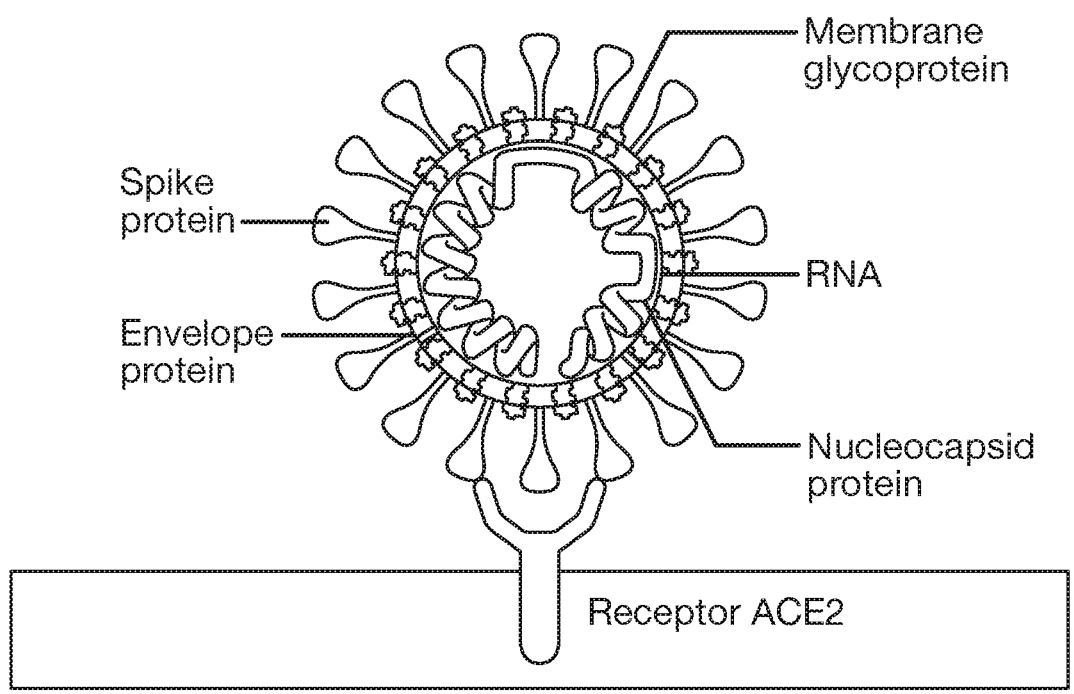
FIG. 1 is an illustration of the coronavirus structure and viral receptor ACE2 on the host cell surface.
Figure 2:
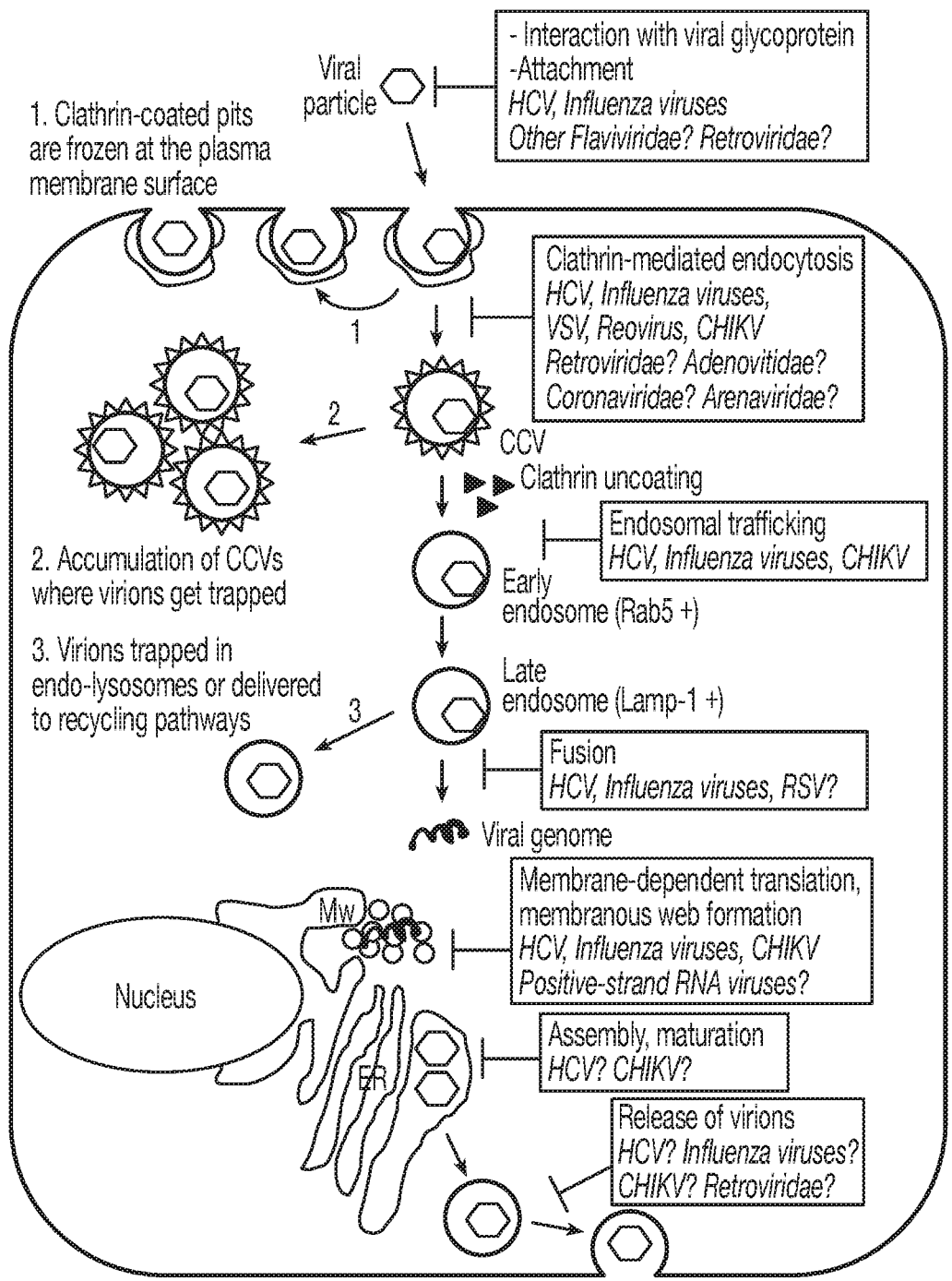
FIG. 2 is an illustration showing broad-spectrum activity of arbidol and its molecular mechanisms of action at the cellular level.
Figure 3:
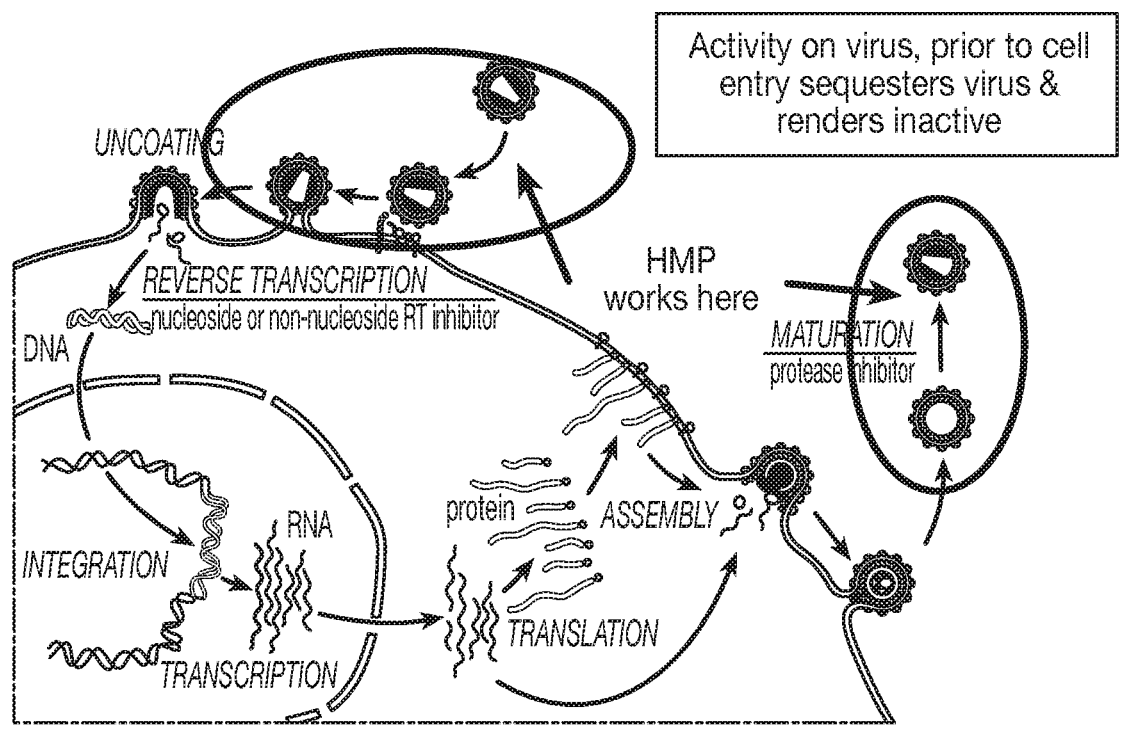
FIG. 3 is an illustration showing the polymers of the invention may show activity against COVID-19 by inhibiting entry of the virus in a host cell.

As used herein, the term "infectable surface" means a surface of a living animal the cells of which may be infected by a virus, including mammals such as human beings. Examples of such infectable surfaces are external skin tissues and mucosal tissues. Mucosal tissues include oral, ocular, nasal, vaginal and rectal tissue.

As used herein, the term "ingestible surface" refers to the surface of foods, including the surface of fruits and vegetables. As used herein, the term "hard surface" refers to surfaces found in the environment such as tables, chairs, walls, and other inanimate surfaces with which skin and/or mucosal tissue may come into contact and on which viruses may reside. The term "internal surface" refers to internal organ surfaces within the body of a living organism.

As used herein, the term "virus" means a small infectious agent that can replicate only inside the living cells or organisms. Virus particles contain the following parts: genetic material made from either RNA or DNA and a protein coat that protects the genetic material. In some cases, virus particles are surrounded by an envelope of lipids around the protein coat when the virus particles are outside a cell. Virus particles that contain such an envelope of lipids are referred to herein as "enveloped viruses". Enveloped viruses may include the following organisms: poxviridae including, but not limited to, molloscum contagiosum, chickenpox, smallpox and other pox viruses; Coronaviridae; Flaviviridae Herpesviridae including herpes simplex virus 1 and herpes simplex virus 2; Retroviridae including Lentivirus including Human Immunodeficiency Virus.

As used herein, the term "surfactant" is a surface active agent, or a substance that, when dissolved in water or an aqueous solution, reduces its surface tension or the interfacial tension between it and another liquid.

As used herein, the term "inhibiting transmission" means one or more of the following: (i) impeding the entry of a virus into a host cell; (ii) substantially stopping the introduction of a virus from one individual, infectable surface or contact surface to another; and/or (iii) reducing damage to mucosal membranes such that the membranes retain their integrity and protect against infection by the virus.

As used herein, the hydrophilic-lipophilic balance ("HLB") is a measure of the degree to which a surfactant is hydrophilic or lipophilic, as determined by calculating values for different regions of the surfactant molecule in accordance with methods known to those of skill in the art.

Preferably, the method of this invention relates to a method of inhibiting entry of enveloped viruses into cells comprising, consisting essentially of and consisting of contacting said viruses with an anti-viral composition comprising, consisting essentially of and consisting of at least one low molecular weight hydrophobically modified polymer in an amount effective to inhibit entry of viruses into cells. The methods of this invention further include the application of the compositions set forth herein onto infectable surfaces as well as onto ingestible surfaces. The methods further include contacting viruses with the anti-viral compositions of this invention.

The methods of this invention also include the application of the compositions of this invention to ingestible surfaces such as food as well as to hard surfaces into which skin and mucosal tissue might come into contact. As such, the presence of the compositions of this invention would work to inhibit entry of viruses present on ingestible and hard surfaces into cells contained on skin, mucosa and internal organs.

Preferably, the compositions of this invention contain at least about 55% water.

The compositions of this invention may contain surfactant having an Hydrophilic-Lipophilic Balance (hereinafter, "HLB") greater than about 12. We would expect that said compositions containing less than about 9% by weight of surfactant having an HLB of greater than about 12 would be preferably for use in the methods of this invention. More preferably, the compositions of this invention should contain between about 0.375% and about 9% by weight of surfactant and, most preferably, between about 0.375% and about 6%, even more preferably, between about 0.375% and about 3% by weight of surfactant having an HLB of greater than about 12. More preferably, the HLB should be greater than about 16. Notwithstanding the foregoing, the compositions of this invention may additionally contain surfactants having an HLB of less than 16. The surfactant levels of the compositions of this invention should be sufficiently low so as not to produce irritation of the skin of a mammal upon exposure or tissue disruption to the cells of the skin or mucosa of said mammal. Such tissue disruption results in providing easier viral entry into the cells. Nonetheless, compositions capable of being used for cleansing as well as virus inhibition are desirable for application to living organisms, including mammals and preferably, humans.

Preferably, the ratio of surfactant to polymer contained in the compositions of this invention should fall from about 0.125 to less than about 18:1. More preferably, the ratio should be between about 0.125 to about 7.5:1. Most preferably, the ratio should be between about 0.125 to about 3:1.

Thus, the compositions useful in the methods of this invention have a Trans-Epithelial Permeability (hereinafter, "TEP"), as described below, of at least about 3.8.

The compositions of this invention may be applied to infectable surfaces of a living entity including mammals, reptiles, birds, fish, bacteria, and the like. Infectable surfaces of these living entities may include, but are not limited to, skin, mucosal internal tissues. Mucosal tissue includes, but is not limited to oral tissue, ocular tissue, nasal tissue, vaginal tissue, rectal tissue or a combination thereof. Importantly, the compositions and methods of this invention do not disrupt these biological surfaces or cause significant irritation of those surfaces.

Polymeric Material

Examples of polymeric materials useful in the compositions and methods of this invention include low-molecular weight acrylic, polysaccharide, cellulose, starch polymers, other ethylenically-unsaturated polymers, polyesters, polycarbonates, polyanhydrides, polyamides, polyurethanes, polyureas, polyimides, polysulfones, polysulfides, combinations of two or more thereof, and the like. Examples of suitable low molecular weight acrylic polymers include hydrophobically-modified acrylic, polysaccharide, cellulose, starch polymers, combinations of two or more thereof, and the like. Suitable low molecular weight acrylic polymers include hydrophobically-modified acrylic polymers, as well as other acrylic polymers, any of which may be formed via solution, suspension, precipitation, dispersion, emulsion, inverse emulsion, microemulsion, micellar polymerization methods, and combinations of two or more thereof. The acrylic polymers for use in the present invention may be derived from any one or more monomers selected from the group consisting of (meth)acrylates, (meth)acrylamides, vinyl ethers, esters, and amides, allyl ethers, esters, amines, and amides, itaconates, crotonates, styrenics, and olefins. The acrylic polymers may be nonionic hydrophilic, nonionic hydrophobic, anionic, cationic, zwitterionic, nonassociative macromer, associative macromer, or multifunctional/cross-linking.

As used herein the term "low molecular weight" polymer refers to a polymer having a number average molecular weight ($M_n$) of about 100,000 or less as measured by gel permeation chromatography (GPC) calibrated with a poly (methyl methacrylate) (PMMA) standard. In certain preferred embodiments, low-molecular weight polymers are those having molecular weight ranges of from about 5,000 to about 80,000 $M_n$, more preferably from about 10,000 to about 50,000 $M_n$, and more preferably between about 15,000 and 40,000 $M_n$.

Certain hydrophobically-modified polymers and methods of making such polymers are described in U.S. Pat. No. 6,433,061, issued to Marchant et al. and incorporated herein by reference. The polymeric materials useful in the composition of this invention are preferably non-crosslinked, linear acrylic copolymers that are very mild to the skin and mucosa. These non-crosslinked, linear polymers are preferably of low molecular weight having a number average molecular weight of 100,000 or less as measured by gel permeation chromatography (GPC) calibrated with a poly (methyl methacrylate) (PMMA) standard (as used herein, unless otherwise specified, all number average molecular weights ($M_n$) refer to molecular weight measured in such manner). Thus, the polymeric material functions as a copolymeric compound. The copolymeric compound is polymerized from at least two monomeric components. The first monomeric component is selected from one or more α,β-ethylenically unsaturated monomers containing at least one carboxylic acid group. This acid group can be derived from monoacids or diacids, anhydrides of dicarboxylic acids, monoesters of diacids, and salts thereof. The second monomeric component is hydrophobically modified (relative to the first monomeric component) and is selected from one or more α,β-ethylenically unsaturated non-acid monomers containing a $C_1$ to $C_9$ alkyl group, including linear and branched $C_1$ to $C_9$ alkyl esters of (meth)acrylic acid, vinyl esters of linear and branched $C_1$ to $C_{10}$ carboxylic acids, and mixtures thereof. In one aspect of the invention the second monomeric component is represented by the formula:

$$CH_2=CRX$$

wherein R is hydrogen or methyl; X is —C(O)OR$^1$ or —OC(O)R$^2$; R$^1$ is linear or branched $C_1$ to $C_9$ alkyl; and R$^2$ is hydrogen or linear or branched $C_1$ to $C_9$ alkyl. In another aspect of the invention R$^1$ and R$^2$ is linear or branched $C_1$ to $C_8$ alkyl and in a further aspect R$^1$ and R$^2$ are linear or branched $C_2$ to $C_5$ alkyl.

Thus, preferably the hydrophobically modified polymers useful in the compositions and methods of this invention comprise, consist essentially of and consist of a polymer derived from at least one first monomeric component selected from the group consisting of (meth)acrylic acid and at least one second monomeric component selected from the group consisting of one or more $C_1$ to $C_9$ alkyl (meth) acrylates, wherein the low molecular weight copolymer has a number average molecular weight of about 100,000 or less.

Exemplary first monomeric components include (meth) acrylic acid, itaconic acid, citraconic acid, maleic acid, fumaric acid, crotonic acid, aconitic acid, and mixtures thereof. Exemplary second monomeric components include ethyl(meth)acrylate, butyl(meth)acrylate, 2-ethylhexyl (meth)acrylate, vinyl formate, vinyl acetate, 1-methylvinyl acetate, vinyl propionate, vinyl butyrate, vinyl 2-ethylhexanoate, vinyl pivalate, vinyl neodecanoate, and mixtures thereof. As used herein, the terms "(meth)acrylic" acid and "(meth)acrylate" are meant to include the corresponding methyl derivatives of acrylic acid and the corresponding alkyl acrylate For example, "(meth)acrylic" acid refers to acrylic acid and/or methacrylic acid and "(meth)acrylate" refers to alkyl acrylate and/or alkyl methacrylate.

More preferably, said first monomeric component is selected from the group consisting of (meth)acrylic acid and said second monomeric component is selected from the group consisting of at least one $C_1$ to $C_9$ alkyl(meth)acrylate.

The non-crosslinked, linear acrylic copolymer compounds useful in the compositions and methods of this invention can be synthesized via free radical polymerization techniques known in the art. In one aspect of the invention, the amount of the first monomeric component to the second monomeric component utilized ranges from about 20:80 wt. % to about 50:50 wt. %, based on the total weight of all of the monomers in the polymerization medium. In another aspect the weight ratio of the first monomeric component to the second monomeric component is about 35:65 wt. %, and in a further aspect the weight ratio of first monomeric component to second monomeric component is about 25:75 wt. %, all based on the total weight of all monomers in the polymerization medium.

Methods of synthesizing the polymers useful in the compositions and methods of this invention may be found in U.S. Pat. No. 6,433,061 which is hereby incorporated herein by reference.

The linear copolymeric materials useful in the methods and compositions of this invention preferably have a viscosity of 500 mPa·s or less (Brookfield RVT, 20 rpm, spindle no. 1) at a 5 wt. % polymer solids concentration in deionized water and neutralized to pH 7 with an 18 wt. % NaOH solution. The viscosity can range from about 1 to about 500 mPa·s in another aspect, from about 10 to about 250 mPa·s in a further aspect, and from about 15 to about 150 mPa·s in a still further aspect.

Preferably, the low molecular weight, non-crosslinked linear acrylic copolymer present in the compositions and methods of this invention is potassium acrylates copolymer.

The low molecular weight hydrophobically modified polymers useful in the compositions and methods of this invention are preferably present in said compositions in amounts that are effective to inhibit substantially the entry of enveloped viruses into cells and/or to inhibit virus transmission to cells. Accordingly, the compositions and methods of this invention inhibit virus entry into said cells and results in the reduction of the potential for viral infection. Preferably, they should be present in the compositions of this invention in an amount of from about 0.00005% to about 10% percent by weight of the composition. Even more preferably, they should be present in the amount of from about 0.00005% to about 3% by weight of the composition. More preferably, the low molecular weight hydrophobically modified polymers are present in an amount of from about 0.00005% to about 0.5 percent by weight of the composition. Most preferably, the low molecular weight hydrophobically modified polymers are present in an amount of from about 0.00005% to about 0.01% percent by weight of the composition.

The compositions of this invention may be in the form of a lotion or liquid capable of being applied on the surface of the skin or on an inanimate surface that can contain viruses or bacteria. It may also be a composition which is applied to a mucosal surface such as the surfaces of the nasal cavity or vaginal cavity and can be used as a vaginal microbicide. These types of composition may be more viscous and may be based on a gel formation. The compositions of this invention may be coated onto an absorbent article such as a vaginal or nasal tampon for placement in contact with mucosal surfaces to inhibit viruses in such biologic environments. The compositions of this invention may also be formulated in such a delivery form that they may be injected into the body at appropriate sites where viruses may reside on internal surfaces.

The compositions of this invention may be made into a wide variety of product types that include but are not limited to liquids, lotions, creams, gels, sticks, sprays, shaving creams, ointments, cleansing liquid washes and solid bars, shampoos, pastes, powders, mousses, wipes, patches, wound dressing and adhesive bandages, hydrogels and films. These product types may contain several types of cosmetically acceptable topical carriers including, but not limited to solutions, emulsions (e.g., microemulsions and nanoemulsions), gels, solids and liposomes. The following are non-limiting examples of such carriers. Other carriers may be formulated by those skilled in the art of formulating such product types.

Preferred compositions of the invention include polymer containing gels; polymer containing drops, including, e.g., eye drops; polymer containing contact lens solutions; polymer containing sprays, e.g., face/body sprays, nasal sprays, and mouth and throat sprays; and polymer containing inhalants.

The compositions of the invention may also be used as a coating on or in personal protective equipment. Personal protective equipment, which is commonly referred to as "PPE", is any equipment worn to minimize exposure to a variety of hazards. Examples of PPE include full body suits, gloves, gowns, masks, respirators and eye and foot protection.

The topical compositions useful in the methods of this invention may be formulated as solutions. Solutions preferably contain an aqueous solvent (e.g., from about 50% to about 99.99% or from about 90% to about 99% of a cosmetically acceptable aqueous solvent).

Topical compositions useful in the methods of this invention may be formulated as a solution containing an emollient. Such compositions preferably contain from about 2% to about 50% of an emollient(s). As used herein, "emollients" refer to materials used for the prevention or relief of dryness, as well as for the protection of the skin. A wide variety of suitable emollients is known and may be used herein. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., $7^{th}$ Edition, 1997) (hereinafter "ICI Handbook") contain numerous examples of materials for use in the compositions and methods of this invention.

A lotion may also be made from such a solution. Lotions preferably contain from about 1% to about 20% (more preferably, from about 5% to about 10%) of an emollient(s) and from about 50% to about 90% (more preferably, from about 60% to about 80%) of water.

Another type of product that may be formulated from a solution is a cream. A cream preferably contains from about 5% to about 50% (more preferably, from about 10% to about 20%) of an emollient(s) and from about 45% to about 85% (more preferably from about 50% to about 75%) of water.

Yet another type of product that may be formulated from a solution is an ointment. An ointment may contain a simple base of animal or vegetable oils or semi-solid hydrocarbons. An ointment may preferably contain from about 2% to about 10% of an emollient(s) plus from about 0.1% to about 2% of a thickening agent(s). A more complete disclosure of thickening agents or viscosity increasing agents useful herein may be found in Sagarin, Cosmetics, Science and Technology, 2nd Edition, Vol. 1, pp. 72-73 (1972) and the ICI Handbook pp. 1693-1697.

The topical compositions useful in the methods of this invention may also be formulated as emulsions. If the carrier is an emulsion, preferably from about 1% to about 10% (e.g., from about 2% to about 5%) of the carrier contains an emulsifier(s). Emulsifiers may be nonionic, anionic or cationic. Suitable emulsifiers are set forth in, for example, U.S. Pat. Nos. 3,755,560, 4,421,769, McCutcheon's Detergents and Emulsifiers, North American Edition, pp. 317-324 (1986), and the ICI Handbook, pp. 1673-1686, which are incorporated herein by reference.

Lotions and creams may also be formulated as emulsions. Preferably such lotions contain from 0.5% to about 5% of an emulsifier(s). Such creams would preferably contain from about 1% to about 20% (more preferably, from about 5% to about 10%) of an emollient(s); from about 20% to about 80% (more preferably, from 30% to about 70%) of water; and from about 1% to about 10% (more preferably, from about 2% to about 5%) of an emulsifier(s).

Other compositions useful in the methods of this invention include gels and liquid compositions that may be applicable to mucosal surfaces for inhibiting viral transmission. Mucosal surfaces include but are not limited to the vagina, rectum, nasal passages, mouth and throat. Preferably, such compositions should include at least one polyhydric alcohol, including glycerin, polyethylene glycol, propylene glycol, sorbitol or a combination thereof. Other polyhydric alcohols know to those of ordinary skill in the art may be used in the compositions and methods of this invention, including polyethylene glycols ranging from molecular weight of from about 300 to about 1450. Preferably, there should be from about 0.1 to about 50% by weight of glycerin and from about 2 to about 40% by weight of propylene glycol.

The mucosal compositions of this invention should also contain one or more water-soluble cellulose-derived polymers. Preferably, such polymers should be a cellulose gum such as one or more hydroxyalkylcellulose polymer. More preferably, the hydroxyalkylcellulose polymer should be one or more of hydroxyethylcellulose, hydroxymethylcellulose, hydroxypropylcellulose, hydroxypropylmethylcellulose and the like. Preferably, the cellulose-derived polymer should be present in the compositions of this invention in the amount of from about 0.1 to about 2% by weight of the composition.

Preferably, an inorganic base may be used to adjust the pH of the composition to be compatible with the vaginal, oral or rectal mucosa. Potassium hydroxide or another alkali metal or alkaline earth metal base may be useful to provide the appropriate pH. Of course, any other physiological acceptable base may also be used in this manner. From about 0.05 to about 5% by weight inorganic base is preferably used.

The compositions of this invention may be prepared in accordance with those methods and processes known to those of skill in the art, or in accordance with the methods of preparation of this invention. For example, water-soluble components such as glycerin, propylene glycol, sorbitol, inorganic base, preservatives, and the like may be dissolved in water and to that combination cellulose-derived polymers may be added. Another method of preparation is mixing all the ingredients into a slurry without water, and then adding the slurry to water.

The compositions of this invention may be wash-off cleansing composition preferably containing a low level of surfactant as set forth above, including anionic, cationic, amphoteric, or nonionic surfactants. Such surfactants contained in the compositions of this invention include those set forth in copending U.S. patent application Ser. No. 12/822,329 (filed Jun. 24, 2010), Ser. No. 12/976,573 (filed Dec. 22, 2010) and Ser. No. 13/166,445 (filed Jun. 22, 2011). Surfactants that are preferable for use in the compositions of this invention include, but are not limited to: anionic types, including: alkyl carboxylates; alkyl sulfonates; alkyl ether sulfonates; alkylbenzenesulfonates; naphthalenesulfonates; olefin sulfonates; alkyl sulfates; alkyl sulfonates; sulfated natural oils & fats; sulfated esters; sulfated alkanolamides; alkylphenols, ethoxylated & sulfated; nonionic types, including ethoxylated aliphatic alcohol; polyoxyethylene surfactants; carboxylic esters of fatty acid; alkyl polyethylene glycol esters; glycol esters of fatty acids; carboxylic amides; monoalkanolamine condensates; polyoxyethylene fatty acid amides; cationic types, including dodecyl trimethyl ammonium chloride (15), cetyl ethyl morpholinium ethosulphate(25-30), polyethoxylated c12 amine (15 mol ethylene oxide), polyethoxylated c18 amine (15 mol ethylene oxide); quaternary ammonium salts; amines with amide linkages; polyoxyethylene alkyl & alicyclic amines; N,N,N',N' tetrakis substituted ethylenediamines; 2-alkyl 1-hydroxethyl 2-imidazolines, amphoteric types, including N-alkyl 3-aminopropionic acid/sodium salt; N-alkyl 3-iminodipropionate, disodium salt; N-carboxymethyl n dimethyl N-9 octadecenyl ammonium hydroxide; N-cocoamidethyl N hydroxyethylglycine, sodium salt, alkyl amidopropyl betaine salts, alkyl ampho acetate salts and the like.

Preferably, surfactants useful in the compositions and methods of this invention may be selected from but not limited to, the following: Potassium cetyl phosphate, hydrogenated palm glycerides (available from Symrise AG of Branchburg, N.J.), polysorbate 20, 60 and 80 (available from UNIQEMA of Bridgewater, N.J.), 2-methyloxirane and oxirane (available from BASF Corporation of Florham Park, N.J.) and the like.

Compositions containing levels of surfactants higher than about 0.375% by weight of the compositions have been found to cause excessive irritation to mammalian skin and the cells found thereon. In consequence, viral transmission is not substantially inhibited in accordance with the methods of this invention. We theorize that this failure to inhibit viruses when higher amounts of surfactants are present is due to disruption of the cell membranes contained in the skin and/or mucosa, engendering easy entry for the viruses into the cells.

Included in a liquid or lotion formation of the composition may be water, oils, preservatives, emulsifiers, viscosity enhancers, emollients, electrolytes, fragrance, buffers, pH modifiers, skin protectants, metal ion sequestrants and the like.

The compositions of this invention may be useful in formulating hand and/or body washes, fruit and/or vegetable washes, ingestible compositions, suppositories, nasal sprays, post-surgical tampons and the like, which may be applied to surfaces or placed in the body to inhibit transmission of viruses.

Methods

There are various testing methods that have been employed herein to evaluate different aspects of the methods and compositions of this invention and their effects upon skin, mucosa and viruses when exposed to the compositions of the invention. The Trans-Epithelial Permeability ("TEP") test is used in the instant methods and in the following Examples. The TEP test is used to determine the degree to which a composition causes irritation to the skin or mucosa.

Trans-Epithelial Permeability Test ("TEP Test"):

Irritation to the eyes and/or skin expected for a given formulation is measured in accordance with the Invittox Protocol Number 86 (May 1994), the "Trans-epithelial Permeability (TEP) Assay" and set forth in U.S. Pat. No. 7,157,414, which are incorporated herein by reference. In general, the ocular and/or skin irritation potential of a product may be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that leaks through to the lower well after 30 minutes, as determined spectrophotometrically. The fluorescein leakage is plotted against the concentration of test material to determine the $EC_{50}$ (the concentration of test material that causes 50% of maximum dye leakage, i.e., 50% damage to the permeability barrier). Higher scores are indicative of milder formulas.

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma; causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

Evaluation of Activity Against HIV-$1_{IIIB}$ in CEM-SS Cells

Fifty microliters (50 µL) of CEM-SS cells at a density of $2.5 \times 10^3$ cells/well in 10% complete Roswell Park Memorial Institute Medium ("RPMI")-1640 (10% FBS with 1% L-glutamine and 1% Penicillin/Streptomycin, available commercially from Invitrogen located in Carlsbad, Calif.) media are plated in a 96-well round bottom plate. One-hundred microliters (100 µL) of each polymer at 6 concentrations are added in triplicate followed by 50 µL of HIV-$1_{IIIB}$ at a predetermined titer. The cultures are incubated for 6 days at 37° C./5% $CO_2$. Following the incubation, the cells are stained with XTT for evaluation of compound efficacy and cellular toxicity, as described below. AZT is evaluated in parallel as an assay positive control compound.

XTT Staining for Cell Viability and Compound Cytotoxicity:

$TC_{50}$ values for the test materials are derived by measuring the reduction of the tetrazolium dye XTT (2,3-bis(2-methoxy-4-nitro-5-sulfophenyl)-5-[(phenylamino)carbonyl]-2H-tetrazolium hydroxide). XTT in metabolically active cells is metabolized by the mitochondrial enzyme Nicotinamide adenine dinucleotide phosphate oxidase ("NADPH") to a soluble formazan product. XTT solution is prepared daily as a stock of 1 mg/ml in RPMI-1640 without additives. Phenazine methosulfate (PMS) solution is prepared at 0.15 mg/ml in DPBS and stored in the dark at −20° C. XTT/PMS stock is prepared immediately before use by adding 40 µL of PMS per ml of XTT solution. Fifty µL (50 µL) of XTT/PMS is added to each well of the plate and the plate incubated for 4 hours at 37° C. The 4 hour incubation has been empirically determined to be within the linear response range for XTT dye reduction with the indicated numbers of cells for each assay. The plates are sealed and inverted several times to mix the soluble formazan product and the plate is read at 450 nm (650 nm reference wavelength) with a Molecular Devices SpectraMax Plus 384 96 well plate format spectrophotometer.

Materials:

A low molecular weight hydrophobically modified polymer, Potassium Acrylates Copolymer (Lubrizol, Brecksville, Ohio) was used in the compositions of this invention as the low molecular weight hydrophobically modified polymer.

Example 1

Examples B1 and A1: Preparation of Compositions to be Tested

The compositions of B1 and A1 were prepared according to the descriptions set forth below with materials in the amounts listed in Table 1. Composition A1 is in accordance with compositions and methods set forth in co-pending patent application filed concurrently herewith.

TABLE 1

| Ingredient<br>INCI name | B1<br>w/w % | A1<br>w/w % |
|---|---|---|
| Potassium Acrylates Copolymer | 0.50 | — |
| PEG6000 | — | 0.5 |
| Sodium Hydroxide | qs | qs |
| Water | qs | qs |

*expressed in % w/w actives

Each of the compositions of Table 1 was independently prepared as follows:

B1-1.7 g of Potassium Acrylates Copolymer (Activity 30%) was mixed with 98.3 g of deionized water and the pH adjusted to 6.5 using 20% Sodium Hydroxide solution.

A1-0.5 g of PEG6000 was dissolved in water with slight heating and the pH measured was 6.65.

Example 2

Inventive Examples E1-E3: Preparation of Illustrative Embodiments of the Compositions of This Invention Stable anti-viral compositions of E1-E3 were prepared according to the materials and amounts listed in Table 2 and the methods set forth below.

TABLE 2

| INCI name | E1 | E2 | C1 | E3 |
|---|---|---|---|---|
| Potassium Acrylates Copolymer | 0.05 | 3.0 | 0.05 | 3.0 |
| Lauryl Glucoside (unpreserved) | 0.375 | 0.375 | 9.0 | 9.0 |

*expressed in % w/w actives

Each of the embodiment compositions of Table 2 may be independently prepared as follows:

E1—0.498 g of Potassium Acrylates Copolymer (Activity 30%) and 0.5910 g Lauryl Glucoside (Activity 52.5%) were added to 298.911 g of deionized water, mixed and the Potassium Acrylates Copolymer was neutralized using 20% Sodium hydroxide. The final pH measured was 5.98.

E2—30.0 g of Potassium Acrylates Copolymer (Activity 30%) and 0.5910 g Lauryl Glucoside (Activity 52.5%) were added to 269.4090 g of deionized water, mixed and the Potassium Acrylates Copolymer was neutralized using 20% Sodium hydroxide. The final pH measured was 5.98.

C1—0.498 g of Potassium Acrylates Copolymer (Activity 30%) and 51.90 g Lauryl Glucoside (Activity 52.5%) were added to 247.6020 g of deionized water, mixed and the Potassium Acrylates Copolymer was neutralized using 20% Sodium hydroxide. The final pH measured was 5.95.

E3—30.0 g of Potassium Acrylates Copolymer (Activity 30%) and 51.90 g Lauryl Glucoside (Activity 52.5%) were added to 218.10 g of deionized water, mixed and the Potassium Acrylates Copolymer was neutralized using 20% Sodium hydroxide. The final pH measured was 5.94.

Example 3

Mildness Testing via Trans Epithelium Permeation (TEP) Test

Samples of E1, E2, E3 and C1 were tested for TEP as per the method detailed set forth above.

TABLE 3

| Sample | TEP: $EC_{50}$ |
|---|---|
| E1 (0.05 potassium acrylates copolymer + .375 lauryl polyglucoside) | 66.33 ± 13.63 |
| E2 (3% potassium acrylates copolymer + .375 lauryl polyglucoside) | 62.71 ± 6.08 |
| C1 (0.05 potassium acrylates copolymer + 9% surfactant) | 4.90 ± 0.71 |
| E3 (3% EX-968 + 9% lauryl polyglucoside) | 4.09 ± 1.13 |

Example 4

Activity of Embodiments Against HIV-1

Following the protocol described above, embodiments E1-E3, C1, A1 and B1 were tested against HIV-1. (See Table 4).

TABLE 4

| Virus | E1 EC50 (µg/ml) | E2 EC50 (µg/ml) | E3 EC50 (µg/ml) | C1 EC50 (µg/ml) | A1 EC50 (µg/ml) | B3 EC50 (µg/ml) |
|---|---|---|---|---|---|---|
| HIV-1 IIIB | 0.4 | 1.5 | 0.006 | 0.5* | >2500* | >2.5* |

*Formulas are toxic to cells at levels at or below inhibitory concentrations. No activity determined.

What is claimed is:

1. A method of inhibiting entry of enveloped viruses into cells of a subject comprising-applying an anti-viral composition to infectable surfaces of said subject, wherein said infectable surfaces comprise mucosal tissue of said subject, wherein said mucosal tissue comprises tissue selected from the group consisting of oral tissue, ocular tissue, nasal tissue, vaginal tissue, or rectal tissue and a combination thereof, wherein said anti-viral composition comprises at least one low molecular weight hydrophobically modified polymer in an amount effective to inhibit entry of viruses into cells, wherein said enveloped viruses is a Retrovirus,
   wherein said low molecular weight hydrophobically modified polymer is potassium acrylates copolymer,
   wherein said composition comprises from about 0.375% to about 9% by weight of surfactant having an HLB greater than 12,
   wherein said composition comprises a dosage form selected from the group consisting of: a liquid, a lotion, a cream, a gel, a stick, a spray, an ointment, a paste, a powder, a mousse, a wipe, a patch, a hydrogel and a film.

2. A method according to claim 1, wherein said composition comprises between about 0.375% and 6% by weight of surfactant.

3. A method according to claim 1 wherein said composition comprises between about 0.375% and 3% by weight of surfactant.

4. A method according to claim 1 wherein the TEP of said anti-viral composition is greater than about 3.8.

5. A method according to claim 1 wherein said low molecular weight hydrophobically modified polymer is present in said composition in an amount of from about 0.00005% to about 3% percent by weight of the composition.

6. A method according to claim 1 wherein said composition further comprises at least 55% of water.

7. A method according to claim 6 wherein said composition comprises at least 97% of water.

8. A method according to claim 1 wherein said inhibition of virus entry into said cells results in the reduction of potential for viral infection.

9. A method according to claim 1 wherein the anti-viral composition does not substantially disrupt biological surfaces.

10. An anti-viral composition comprising at least one low molecular weight hydrophobically modified polymers in an amount effective to inhibit entry of retrovirusues into cells and at least 55% water, wherein said composition comprises from about 0.375% to about 9% by weight of surfactant having an HLB greater than 12, wherein said low molecular weight hydrophobically modified polymer is potassium acrylates copolymer wherein said composition comprises a dosage form selected from the group consisting of: a liquid, a lotion, a cream, a gel, a stick, a spray, an ointment, a paste, a powder, a mousse, a wipe, a patch, a hydrogel and a film.

11. A method of inhibiting the transmission of retrovirusues comprising applying to non-biological surfaces a composition comprising at least one low molecular weight hydrophobically modified polymers in an amount effective to inhibit entry of viruses into cells wherein said composition comprises from about 0.375% to about 9% by weight of surfactant having an HLB greater than 12, wherein said low molecular weight hydrophobically modified polymer is potassium acrylates copolymer.

12. A method of inhibiting the transmission of retrovirusues comprising applying to infectable surfaces a composition comprising at least one low molecular weight hydrophobically modified polymers in an amount effective to inhibit entry of viruses into cells wherein said composition comprises from about 0.375% to about 9% by weight of surfactant having an HLB greater than 12, wherein said low molecular weight hydrophobically modified is potassium acrylates copolymer.

13. A composition according to claim 12 wherein said composition further comprises from about 0.375% to about 9% by weight of surfactant selected from the group consisting of anionic, cationic, nonionic and amphoteric surfactants.

14. The method of claim 1, wherein the retrovirus is HIV.

* * * * *